United States Patent

Zucherman et al.

[11] Patent Number: 5,904,686
[45] Date of Patent: May 18, 1999

[54] APPARATUS AND METHOD FOR PREPARING A SITE FOR AN INTERBODY FUSION IMPLANT

[76] Inventors: James F. Zucherman, 3035 Pierce St., San Francisco, Calif. 94123; Ken Y. Hsu, 52 Clarendon Ave., San Francisco, Calif. 94114

[21] Appl. No.: 08/975,436

[22] Filed: Nov. 20, 1997

Related U.S. Application Data

[63] Continuation-in-part of application No. 08/673,127, Jul. 1, 1996, Pat. No. 5,700,264.

[51] Int. Cl.⁶ .................................................. A61B 17/14
[52] U.S. Cl. ............................. 606/79; 606/82; 606/170; 606/179
[58] Field of Search ................................ 606/79, 82, 170, 606/179, 61, 90; 623/17

[56] References Cited

U.S. PATENT DOCUMENTS

| | | |
|---|---|---|
| 2,537,070 | 1/1951 | Longfellow . |
| 3,112,743 | 12/1963 | Cochran et al. . |
| 3,848,601 | 11/1974 | Ma et al. . |
| 4,059,115 | 11/1977 | Jumashev et al. . |
| 4,124,026 | 11/1978 | Berner et al. . |
| 4,599,086 | 7/1986 | Doty . |
| 4,714,469 | 12/1987 | Kenna . |
| 4,721,103 | 1/1988 | Freedland . |
| 4,743,256 | 5/1988 | Brantigan . |
| 4,772,287 | 9/1988 | Ray et al. . |
| 4,834,757 | 5/1989 | Brantigan . |
| 4,878,915 | 11/1989 | Brantigan . |
| 4,904,260 | 2/1990 | Ray et al. . |
| 4,961,740 | 10/1990 | Ray et al. . |
| 5,015,247 | 5/1991 | Michelson . |
| 5,015,255 | 5/1991 | Kuslich . |
| 5,026,373 | 6/1991 | Ray et al. . |
| 5,055,104 | 10/1991 | Ray . |
| 5,059,193 | 10/1991 | Kuslich . |
| 5,062,845 | 11/1991 | Kuslich et al. . |
| 5,722,977 | 3/1998 | Wilhelmy ................................ 606/61 |

FOREIGN PATENT DOCUMENTS

| | | |
|---|---|---|
| 2015507 | 1/1991 | Canada . |
| 0 073 177 A2 | 8/1982 | European Pat. Off. . |
| 0 260 222 A2 | 7/1987 | European Pat. Off. . |
| 0 537 060 A1 | 5/1992 | European Pat. Off. . |
| 1961531 | 7/1970 | Germany . |
| 3505567 A1 | 5/1986 | Germany . |
| 283078 | 11/1984 | Spain . |

*Primary Examiner*—Gary Jackson
*Assistant Examiner*—Julian W. Woo
*Attorney, Agent, or Firm*—Fliesler, Dubb, Meyer & Lovejoy LLP

[57] ABSTRACT

An instrument set 120 and method for preparing a site between adjacent bones for insertion of an implant includes an alignment probe 122 with a head end 124 and a cutter 134 which fits over the alignment probe 122. The alignment probe 122 can be appropriately positioned using imaging techniques and then given a quarter turn in order to anchor the head end 124 in the bones at the appropriate depth and with the appropriate alignment. The cutter 134 is then inserted over the alignment probe 122 in order to sever bone and tissue. After this is accomplished, the head end 124 is given another quarter turn freeing itself from the bone, and then the alignment probe 122 and the cutter 134 are removed with the tissue and bone captured therebetween.

18 Claims, 11 Drawing Sheets

APPARATUS AND METHOD FOR PREPARING A SITE FOR AN INTERBODY FUSION IMPLANT

CONTINUATION-IN-PART

The present application is a continuation-in-part of U.S. patent application Ser. No. 08/673,127, filed on Jul. 1, 1996, now U.S. Pat. No. 5,700,264.

FIELD OF THE INVENTION

The present invention is related to instrumentation and a method for preparing a site between adjacent bones for purposes of implanting bone or a device. The device or bone implanted may, for example, be used to fuse the bones together or for other purposes.

BACKGROUND OF THE INVENTION

Currently, success has been found by relieving back pain using procedures which implant devices or bone which allow adjacent vertebrae to be fused together across a disk space. These devices generally have apertures and a central cavity, and are packed with bone chips or other bone growth inducing substances. Upon implantation between adjacent vertebrae, the devices relieve the back pain due to dysfunctional disks or due to other reasons, and at the same time provide a site for fusion. Bone growth from the upper and lower vertebrae proceeds through the apertures of the implanted device, uniting with the bone growth inducing substance so that the upper and lower vertebrae fuse together through and around the implant.

Alternatively, an implant made entirely of bone can be implanted to create an interbody fusion between vertebrae.

A number of procedures are used to accomplish such implants. These procedures include approaches to the spinal column from anterior, posterior, and lateral directions, just to name a few.

Prior to the implantation of a device, the implant site must be prepared. Prior art procedures dictate that the site including adjacent vertebrae and the disk located therebetween, must be exposed. As there are major blood vessels and nerves which are protected by and surround the spinal column, care must be taken so that these are not disturbed. Accordingly, after the site is exposed, sheathing devices are located adjacent to the site. The site preparation procedure can then be carried out inside the sheathing devices in order to protect the adjacent blood vessels and nerves. Historically, these sheathing devices are cylindrical in nature with a front end having prongs which project therefrom. The sheathing device is placed adjacent the upper and lower vertebrae, and spans the disk space. The sheathing device is then tapped so that the projecting prongs engage with the outside faces of the upper and lower vertebrae in order to stabilize the sheathing device relative to the vertebrae. After this is accomplished, a drill bit can be inserted in the sheathing device in order to drill out and remove the disk material and both cortical and cancellous bone. The cortical bone provides the hard outer surface of the vertebral body while the cancellous bone is internal and is softer and porous and provides the passages for the blood supply which nourishes the bone.

Such a site preparation technique has been used successfully in the past, however, it is still desirable to improve upon this procedure and make it safer and easier to perform. For example, with the prior art sheathing device, a purchase must be obtained on the anterior, lateral or posterior facing sides of the upper and lower vertebral bone with the prongs extending from the sheathing device. Accordingly, it is not always possible to obtain and maintain the desired alignment of the sheathing device as the operation is carried out. Also as a sheathing device is needed to encase the drill, the diameter of this instrumentation may be a little larger than desired. Further, by using a drilling operation even though the disk space can be cleared out using appropriate cutting instruments, prior to the drilling operation, the drill bit can still become clogged with fibrous disk material and require cleaning prior to the completion of the site preparation.

Further, in such a procedure there is no mechanism for stopping the forward movement of the drill. The physician relies on indicia marked on the drill or other depth gaging devices for ensuring that the drill does not penetrate too far or remove too much material.

Against this background, there is a continuing need to improve the process of preparing a site for implantation.

SUMMARY OF THE INVENTION

The present invention provides for an improved apparatus and method for preparing a site for an implant (whether a device or bone), and in particular, although not exclusively, an implant for fusing together two adjacent bones such as for example two adjacent vertebrae.

The present invention provides for a instrumentation set having an alignment probe with a head end. The head end fits in the disk space between the two adjacent vertebral bodies and is located at the final depth of the implant. At this point, the head end can be anchored to the upper and lower vertebral bodies through a number of procedures, one of which is by rotating the head end so that it engages the upper and lower vertebral bodies. Alignment of the alignment probe can be checked, both before and after anchoring is accomplished, to ensure that the shaft of the alignment probe is properly aligned with respect to the vertebrae and the disk space.

In order to proceed with the removal of disk material and bone material from the upper and lower vertebrae, a cutter with a distal cutting edge is inserted over the post of the alignment probe. The cutter is positioned adjacent the upper and lower faces of the vertebral bodies and spans the disk space. Once positioned, the cutter can be operated in order to cut through the disk and also the cortical bone of the end plane and into the cancellous bone which lies several millimeters beneath the cortical bone. Forward progress of the cutter is blocked by the outer extremities of the head end so the cutter cannot go further than desired. Once the cutter has reached the outer extremities of the head end, the alignment probe and cutter with the severed bone and disk material can be removed leaving a site which is appropriate for fusion device implantation.

Accordingly, it can be seen that the present invention provides for a safe and efficient mechanism for preparing a site between two bones for purposes of implanting a device or bone therebetween.

As an object of the present invention, an apparatus and method is provided which can be used to securely anchor the apparatus so that proper alignment can be ensured and maintained.

As a further object of the invention, efficient removal of the bone and disk material is accomplished without clogging or requiring additional procedures to free clogged instrumentation.

As yet a further object of the present invention, the correct depth for tissue removal is assured by the instrumentation.

In yet another aspect of the present invention, an instrument set includes an alignment probe mounted on a post. The alignment probe includes a first arm and a second arm with the first arm having a first sharpened tip and the second arm having a second sharpened tip. A first cam surface is located behind the first sharpened tip and a second cam surface is located behind the second sharpened tip. The first and second cam surfaces are for caming the spaced bones further apart as the probe is rotated relative to the bone.

An object of the invention when the probe has first and second cam surfaces is for purposes of a posterior approach to the disc space between adjacent vertebra.

Further objects and advantages of the invention can be obtained from a review of the specification, claims, and the figures.

DETAILED DESCRIPTION OF THE PREFERRED EMBODIMENT

Figure 1:
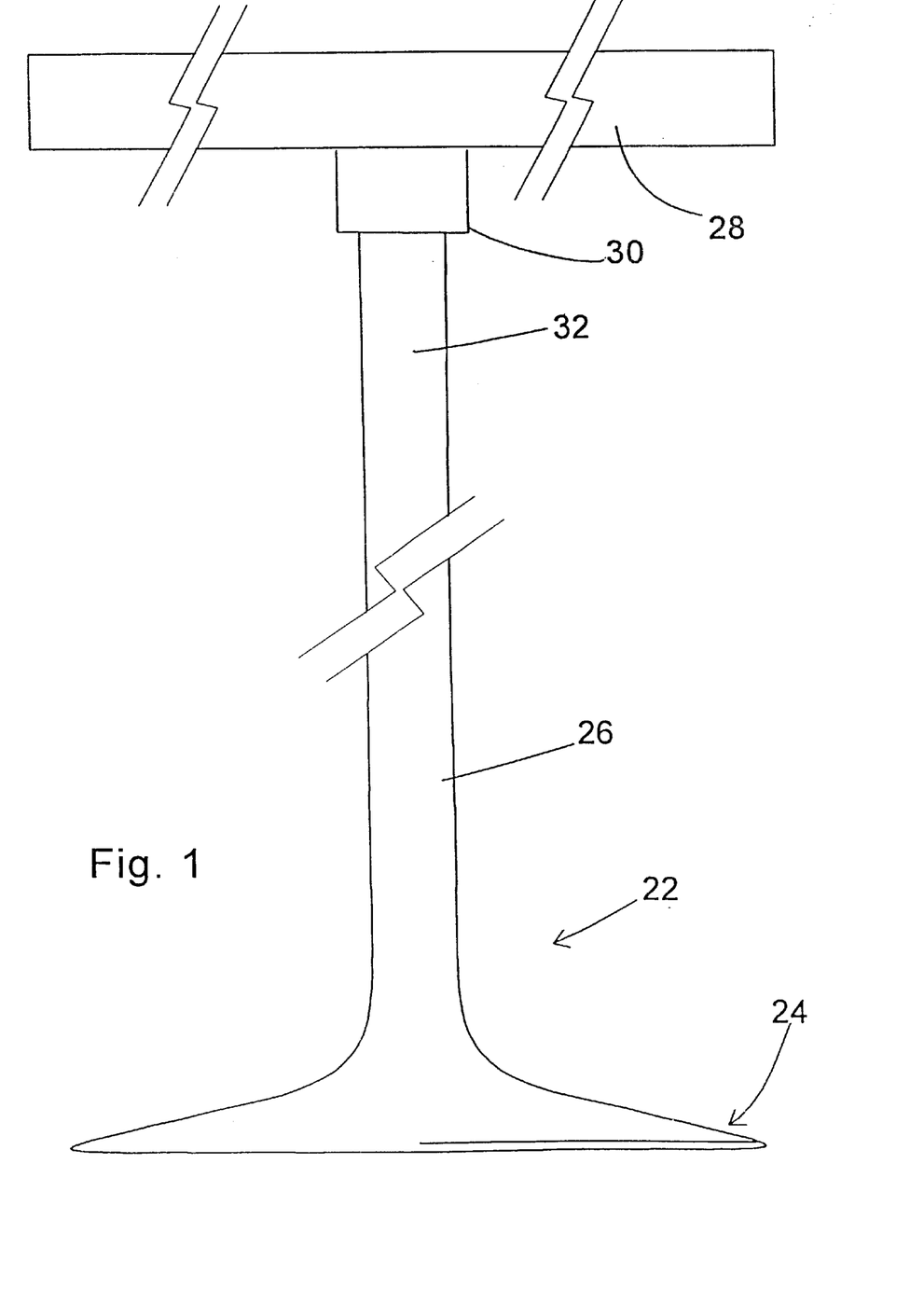
FIG. 1 depicts a side view of the alignment probe of an embodiment of the invention.

Description of the Embodiment of FIGS. 1–11:

In FIG. 1, an alignment probe 22 of the instrument set 20 (FIG. 8) is depicted. Alignment probe 22 includes a front end 24 and a post 26 extending rearwardly from the front end 24. In this embodiment, the alignment probe 22 is essentially T-shaped. The alignment probe 22 is comprised in a preferred embodiment of a medical grade stainless steel which can be sharpened and autoclaved.

The post 26 is preferably cylindrical in shape and extends to a detachable handle 28. Handle 28 is detachable by using a mechanism 30 which is well-known in the art. A set of indicia 32 is marked on the post 26. These indicia 32 are of assistance in determining the depth and location of a cutter 34 (FIG. 8) as it is inserted over the post 26 of the alignment probe 22 as described hereinbelow.

Figure 2:
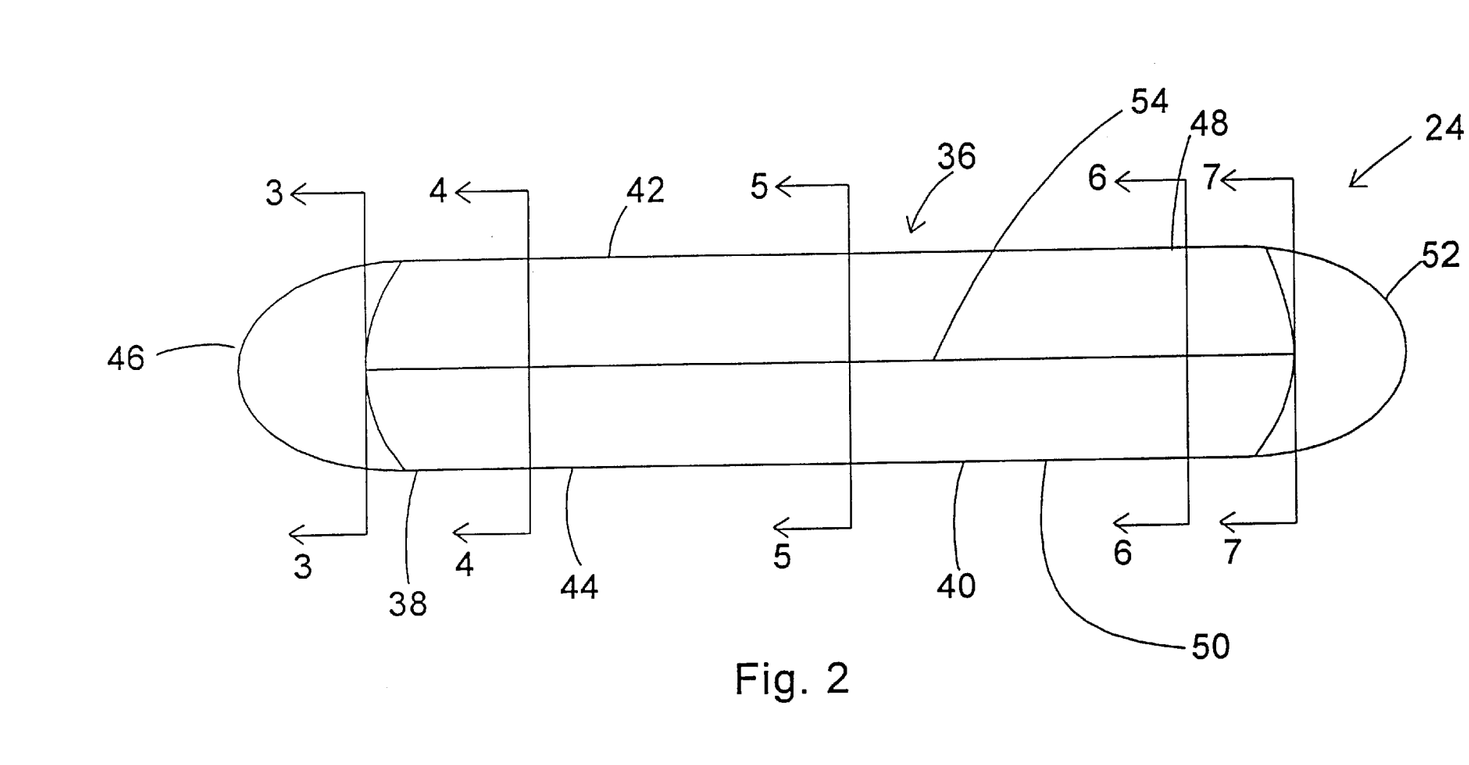
FIG. 2 depicts an end view of one embodiment of the alignment probe of the invention.
Figures 3, 4, 5:
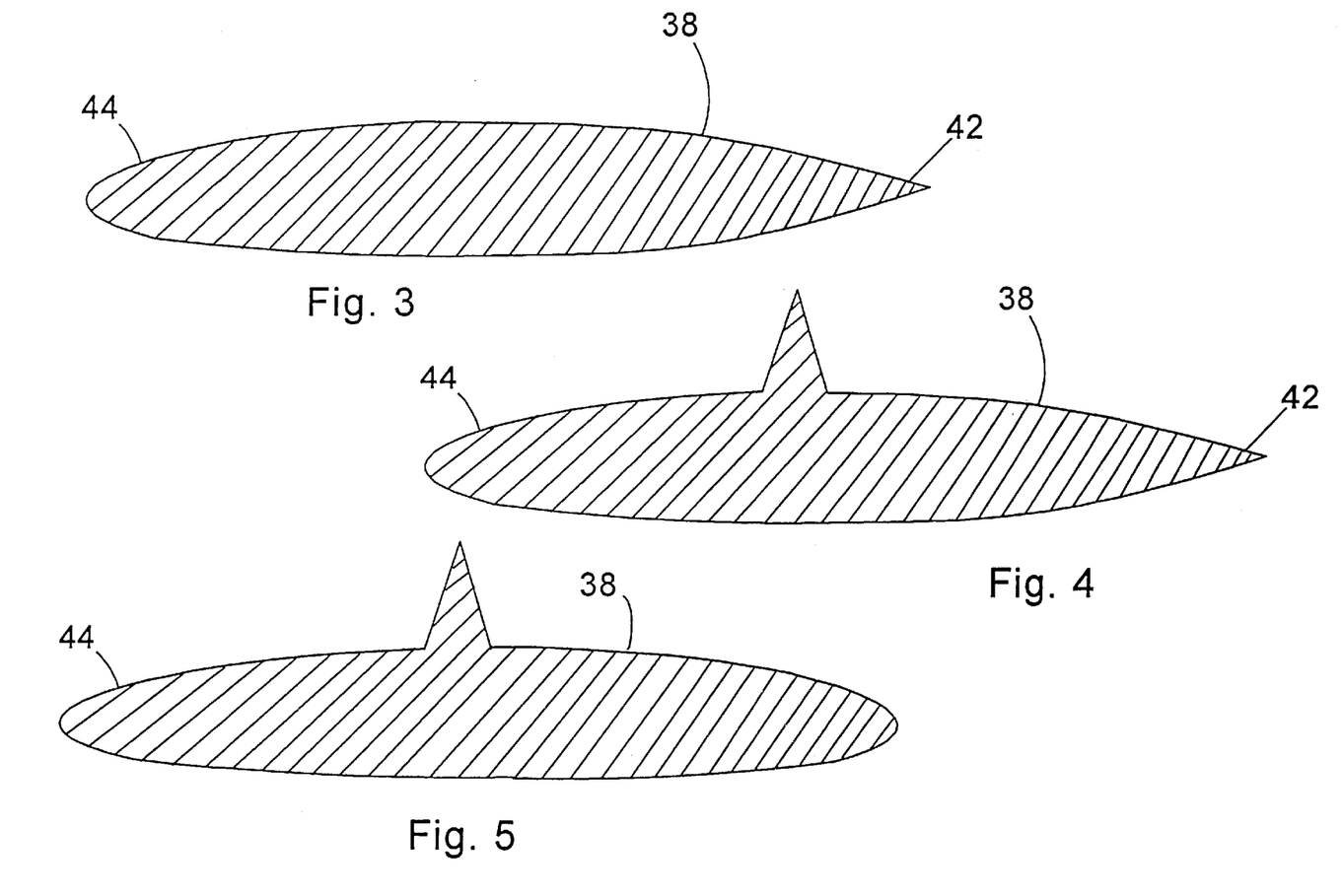
FIG. 3 depicts a cross-sectional view taken through line 3—3 of FIG. 2.
FIG. 4 depicts a cross-sectional view taken through line 4—4 of FIG. 2.
FIG. 5 depicts a cross-sectional view taken through line 5—5 of FIG. 2.
Figure 6:
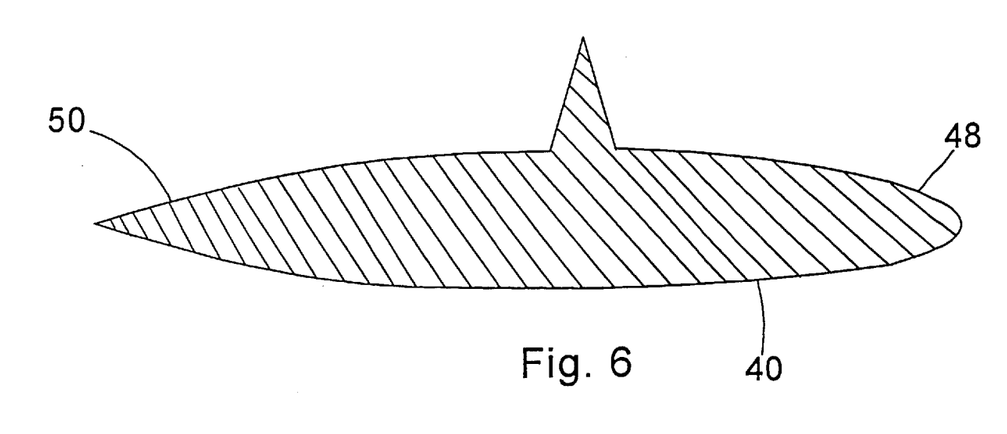
FIG. 6 depicts a cross-sectional view taken through line 6—6 of FIG. 2.
Figure 7:
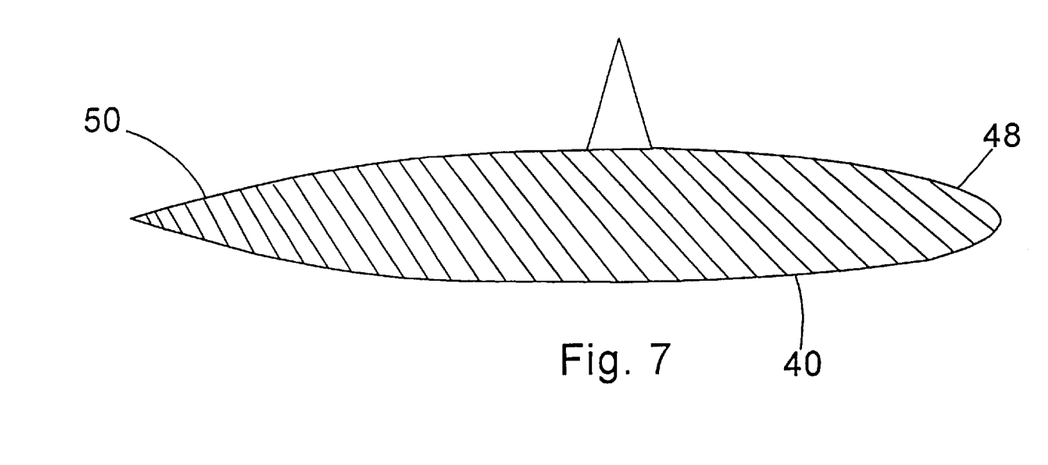
FIG. 7 depicts a cross-sectional view taken through line 7—7 of FIG. 2.

The head end 24 of the alignment probe 22 in this embodiment includes an elongate member 36 which is transversed to post 26 and in particular in this embodiment, perpendicular to the post 26. The head end 24, as can be seen in FIG. 2, includes a first arm 38 and a second arm 40. First arm 38 includes first and second lateral sides 42 and 44, and distal end 46. The second arm 40 includes third and fourth lateral side 48, 50, and distal end 52. In this embodiment, the first lateral side 42 of the first arm 38 merges into and is in line with the third lateral side 48 of the second arm 40. Similarly, the second lateral side 44 of the first arm 38 merge into and is in line with the fourth lateral side 50 of the second arm 40. As can be seen in FIGS. 3, 4, 6 and 7, along most of the length of the first lateral side 42 of the first arm 38 and the fourth lateral side 50 of the second arm 40, the lateral sides have been sharpened in order to be able to penetrate and anchor to the bone at a desired location. In viewing FIGS. 3, 4, 6, and 7 it is noted that the opposite lateral side, that is the second lateral side 44 of the first arm 38 and third lateral side 48 of the second arm 40 is rounded and not sharpened in order to increase the strength of the elongonate member 36. Depending on the materials used and the purpose for the head end 24, only two lateral sides need to be sharpened. In other embodiments, four lateral sides can be sharpened and be within the spirit and scope of the invention.

Projecting forwardly of the head end 24 is a sharpened ridge 54. This ridge can be seen in a cross-section in FIGS. 4, 5 and 6. This ridge projects and extends along the length of the middle of the head end 24 and ends approximately 3 mm to 5 mm of each of the ends 46, 52 of the head end 24. The sharpened ridge 54 is used to cut through disk material located between adjacent vertebrae. The areas of the head end 24 adjacent to ends 46, 52 are not provided with a sharpened ridge 54 as these ends 46, 52 are meant to be rotated into anchoring engagement with the upper and lower vertebral bodies in order to anchor the alignment probe 22 through the cortical bone end plates of the vertebral bodies, and into the cancellous bones in order to secure and position the alignment probe.

It is to be understood that the head end 24 of the alignment probe 22 can come in a variety of lengths. Preferably, head end can be selected in lengths of 13 mm, 17 mm, and 21 mm. These three sized alignment probes 22 can accommodate most situations. For smaller and larger individuals, smaller and larger alignment probes 24 can be fashioned. As it is desirable to penetrate and anchor into about 2 mm to about 3 mm of upper vertebral bone and lower vertebral bone, the sharpened ridge 54 as indicated above, stops short of the ends 46, 52 of the head end 24 by about 3 mm to about 5 mm.

Figure 11:
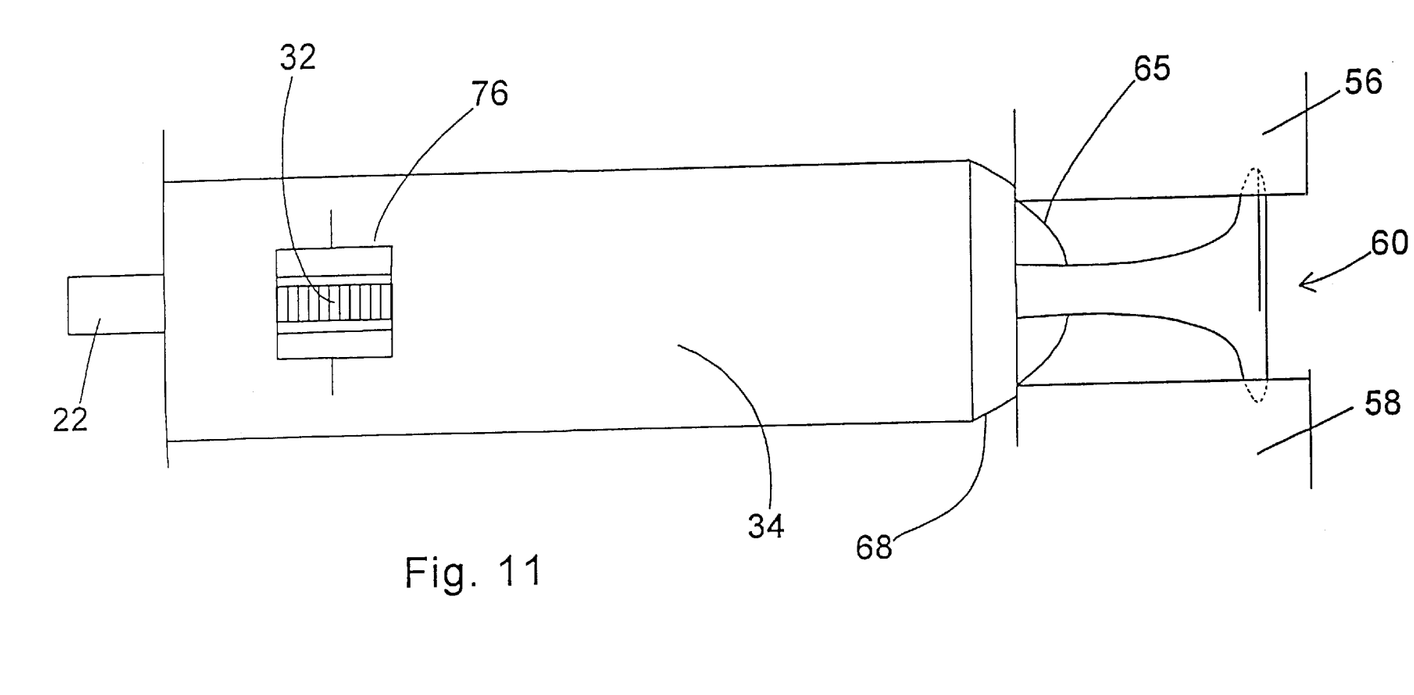
FIG. 11 depicts a side view of the alignment probe of the invention inserted between and anchored to the end plates of adjacent vertebral bodies.

Procedurally, and preferably for an anterior approach, although this probe 22 can also be used for a posterior approach, the vertebrae and the disk located therebetween are exposed and some of the disk material is cut away. The alignment probe 22 is then inserted (FIG. 11) between the end plates of the vertebral bodies 56, 58, which span the disk 60 space. Using appropriate imaging techniques, the probe 22 is viewed to ensure that the depth of the head end 24 is proper and that the post 26 is properly aligned with the disk space and the adjacent vertebrae. The handle 28 is then used to give the head end 24 a quarter turn so that the ends 46, 52 of the head end 24 are anchored in the upper and lower vertebral bone as shown in FIG. 11.

Figure 8:
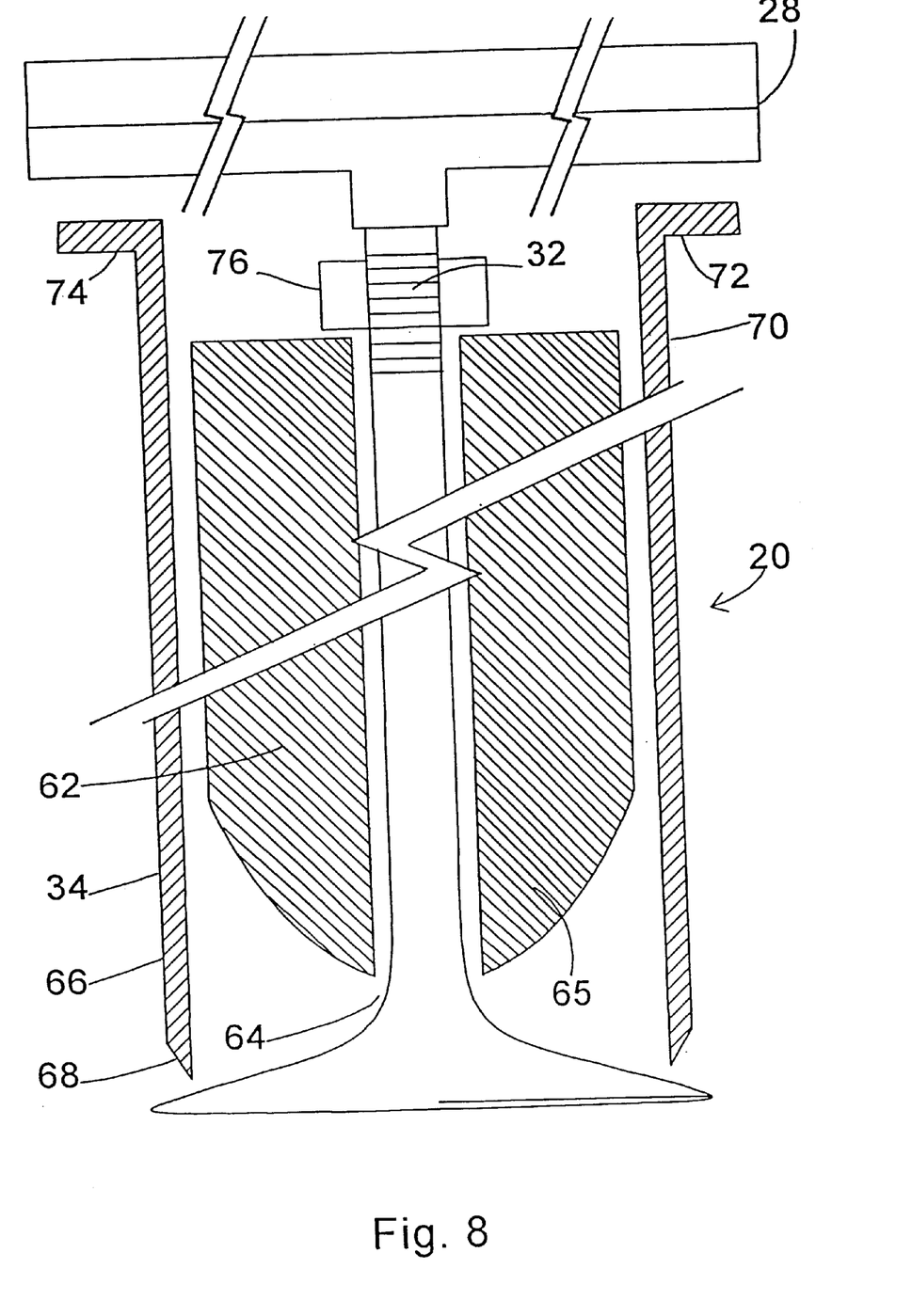
FIG. 8 depicts a partially sectioned cross-sectioned view of the alignment probe, spacer and cutter of the invention.

After this is accomplished, the handle 28 is removed from the post 26 and a cylindrical spacer 62 with a central bore 64 and conically shaped tip 65 is placed over the post 26 as shown in FIG. 8. If desired, the spacer can be tapped into the space between the vertebra in order to distract said vertebra. With the spacer so positioned, cutter 32 can be inserted over the spacer and the post 26 of the alignment probe 22 as shown in FIG. 11 and then positioned against the faces of the vertebral bodies 56 and 58. It is to be understood, that alternatively, the spacer 62 can be incorporated and become an integral part of the cutter 34 and be within the spirit and scope of the invention.

The cutter 34 includes a front end 66 with a sharpened edge 68 and a back end 70 with flanges 72, 74. With the cutter 34 so positioned as seen in FIG. 11, the flanges can be tapped. When this occurs, the cutter cuts through the bone of the upper and lower vertebral bodies and the disk material located therebetween, and proceeds toward the head end 24. The depth of the cutter 34 can be judged by the indicia 32 of the alignment probe 22 as viewed through the window 76 of the cutter 34. The forward motion of the cutter 34 is stopped by gaging the depth of the cutter relative to the indicia 32 or by the sharpened end 68 striking the ends 46, 52 of the head end 24 of the alignment probe 22. After this is accomplished, the alignment probe 22 is given another quarter turn freeing the head end 24 from the upper and lower vertebral bodies. At this point, the entire instrument set including the alignment probe 22 and the cutter 34 can be removed with the bone and disk tissue captured therebetween. An appropriately sized and aligned bore for the insertion of a bone or device implant is then completed.

Figure 9:
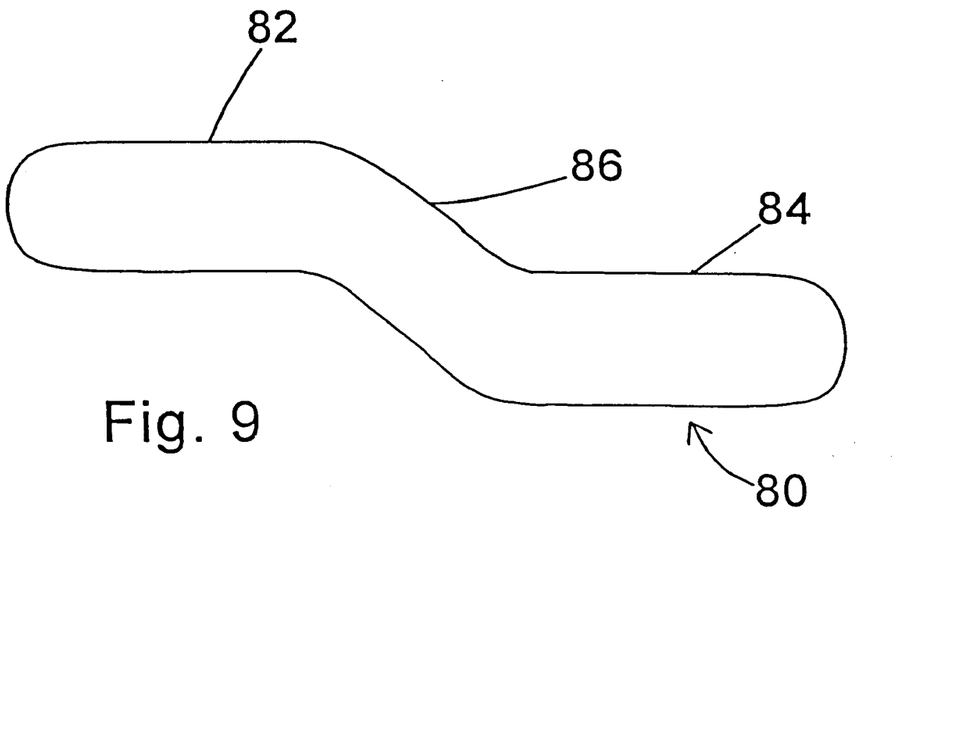
FIG. 9 depicts an alternative embodiment of the head end of the alignment probe.
Figure 10:
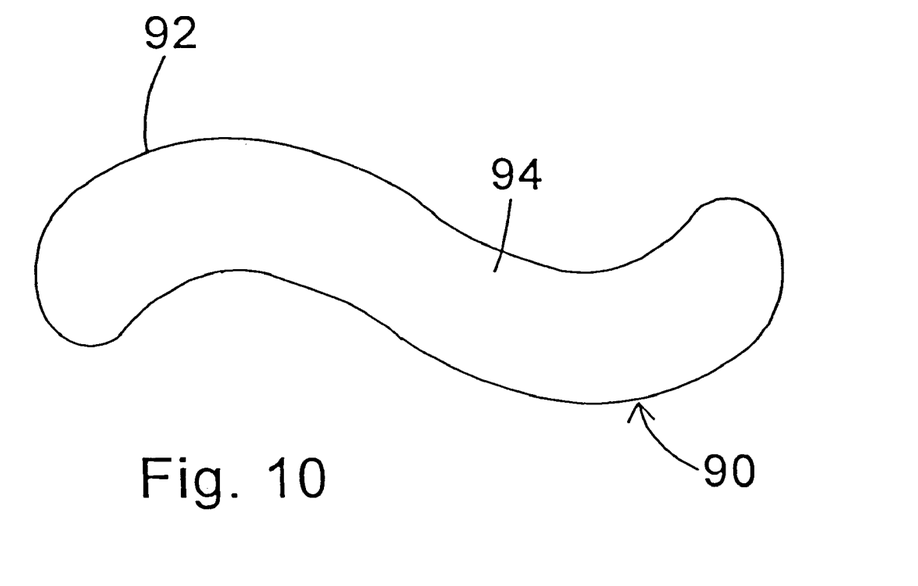
FIG. 10 depicts yet a further alternative embodiment of the head end of the alignment probe.

Alternative embodiments of the invention can be accomplished and be within the spirit and scope of the invention. By way of example only, FIGS. 9 and 10 depict alternative embodiments of the head end 80 and 90 of an alternative alignment probe. It can be seen in FIG. 9 that the head end 80 includes first and second arms 82 and 84 which are staggered about a central hub 86. This head end is Z-shaped and include the advantageous sharpened lateral side as are used with respect to the embodiment of FIG. 2. The height and length of the head end 80 are appropriately sized so that head end 80 can fit in the disk space between adjacent vertebrae.

Another alternative embodiment of the head end 90 of the invention is shown in FIG. 10. In this invention, the arms 92 and 94 are curved much in the design of an sickle. Such a design would require slightly less force to accomplish anchoring due to the sickle nature of the first and second arms 92, 94 in that not all of the cutting edge engages the bone at the same time, as is the case with the embodiments of FIGS. 2 and 9.

It is to be understood that further embodiments of the invention can be accomplished and be within the scope of the invention. By way of example only, the head end could be designed to include a plurality of pins which can be caused to project upwardly and downwardly from the head end using various mechanisms such as for example rack and pinion arrangements, which are actuated by twisting a second post which is disposed internally to the first post. In such an arrangement, the head end is inserted between the vertebral bodies and the pins are then urged out of the head end and into engagement with the upper and lower vertebral body. Such a mechanism does secure the alignment probe relative to the vertebral bodies so that a cutter can be inserted over the post of the alignment probe in order to remove the bone and disk material.

Figure 12:
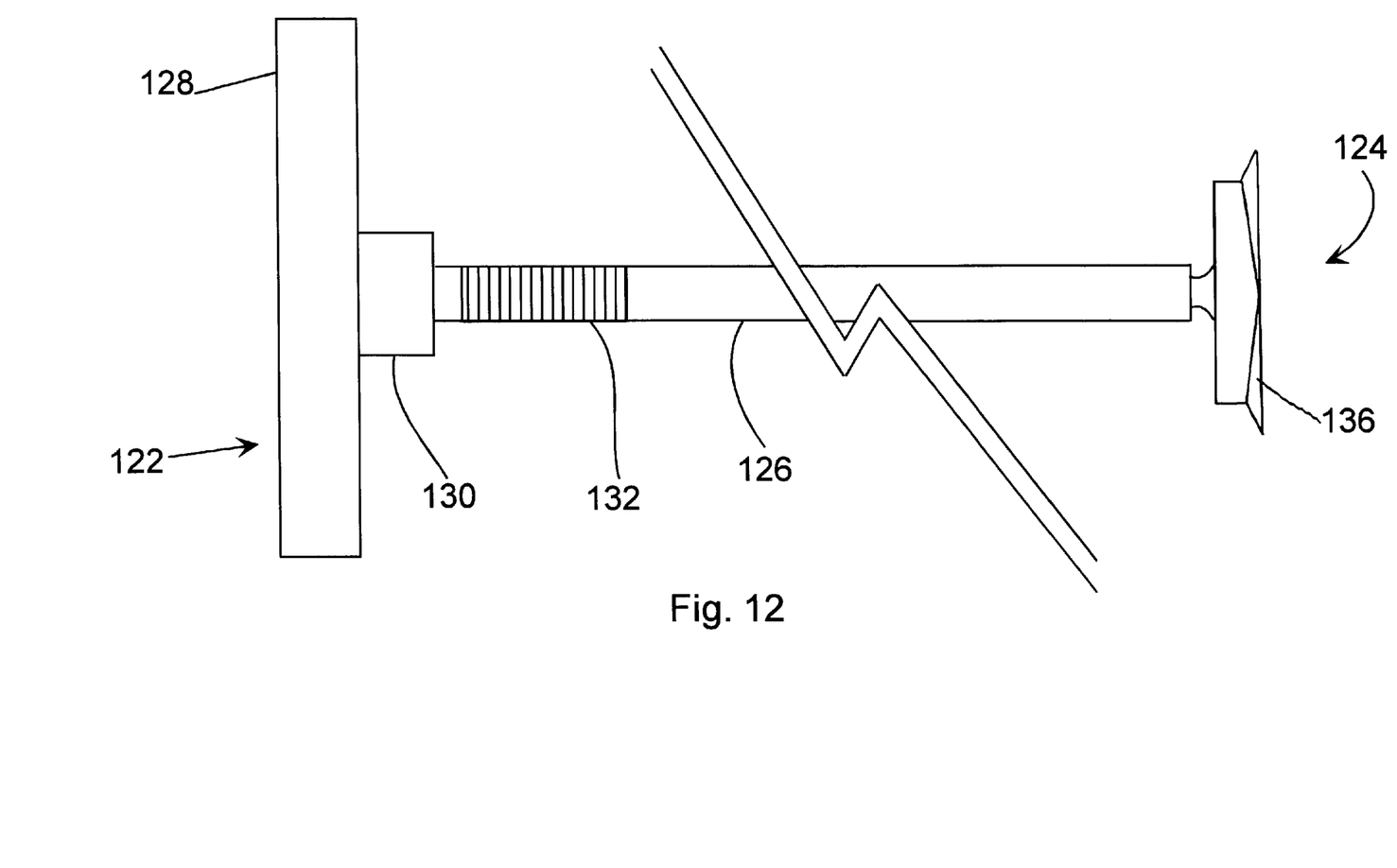
FIG. 12 is a side view of an alternative embodiment of the alignment probe of the present invention.

Description of the Embodiment of FIGS. 12–15:

In FIG. 12, an alignment probe 122 of the instrument set 120 (FIG. 14) is depicted. Alignment probe 122 includes a front end 124 and a post 126 extending rearwardly from the front end 124. In this embodiment, the alignment probe 122 is essentially T-shaped. The alignment probe 122 is comprised in a preferred embodiment of a medical grade stainless steel which can be sharpened and autoclaved.

The post 126 is preferably cylindrical in shape and extends to a detachable handle 128. Handle 128 is detachable by using a mechanism 130 which is well-known in the art. A set of indicia 32 is marked on the post 126. These indicia 32 are of assistance in determining the depth and location of a cutter 34 (FIG. 14) as it is inserted over the post 126 of the alignment probe 122 as described hereinbelow.

Figure 13A:
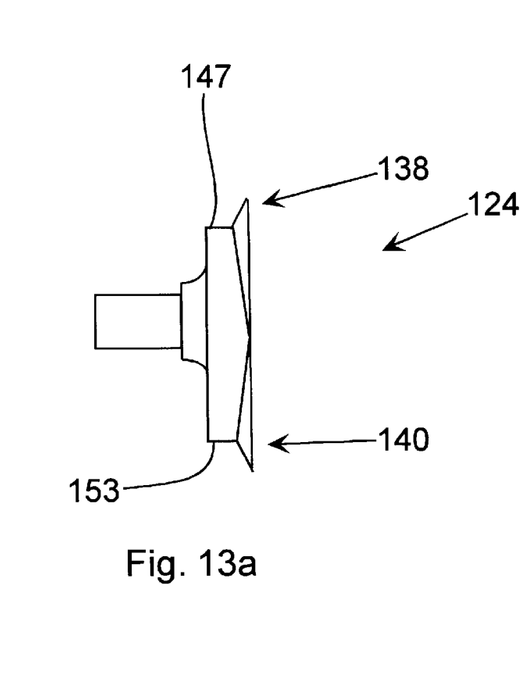
FIGS. 13a, 13b, and 13c are side and left and right views of the front end of the alignment probe of FIG. 12.
Figure 13B:
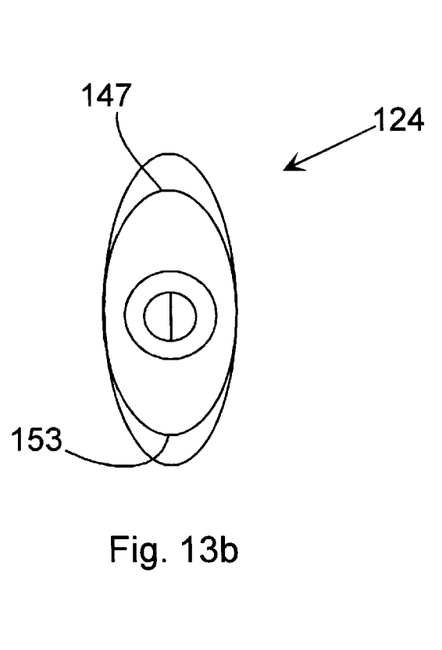
Figure 13C:
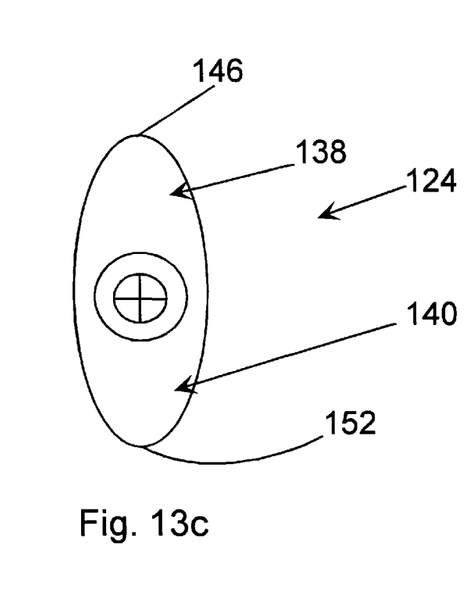

The head end 124 of the alignment probe 122 in this embodiment includes an elongate member 136 which is transversed to post 126 and in particular in this embodiment, perpendicular to the post 126. The head end 124 is substantially elliptically-shaped in this particular embodiment. Other shapes are in the spirit and scope of the invention. The head end 124, as can be seen in FIGS. 13*a*, 13*b*, 13*c*, includes a first arm 138 and a second arm 140. The first arm 138 includes a first sharpened distal tip 146, and the second arm 140 includes a second sharpened distal tip 152. Located behind the first sharpened tip 146 is a first cam surface 147 and located behind the second sharpened tip 152 is a second cam surface 153. These cam surfaces 147, 153 are elliptical in this preferred embodiment. Other cam surface shapes are within the spirit and scope of the invention. These cam surfaces 147, 153 are used to distract adjacent bones as described below. The tips 146, 152, are sharpened in order to be able to penetrate and anchor to the bone at a desired location. The ends 146, 152 are meant to be rotated into anchoring engagement with the upper and lower vertebral bodies in order to anchor the alignment probe 122 through the cortical bone end plates of the vertebral bodies, and into the cancellous bones in order to secure and position the alignment probe.

It is to be understood that the head end 124 of the alignment probe 122 can come in a variety of lengths. Preferably, head end can be selected in lengths of 13 mm, 17 mm, and 21 mm. These three sized alignment probes 122 can accommodate most situations. For smaller and larger individuals, smaller and larger alignment probes 124 can be fashioned. As it is desirable to penetrate and anchor into about 2 mm to about 3 mm of upper vertebral bone and lower vertebral bone, the cam surfaces 147, 153 preferably stop short of the ends 146, 152 of the head end 124 by about 3 mm to about 5 mm.

Figure 15:
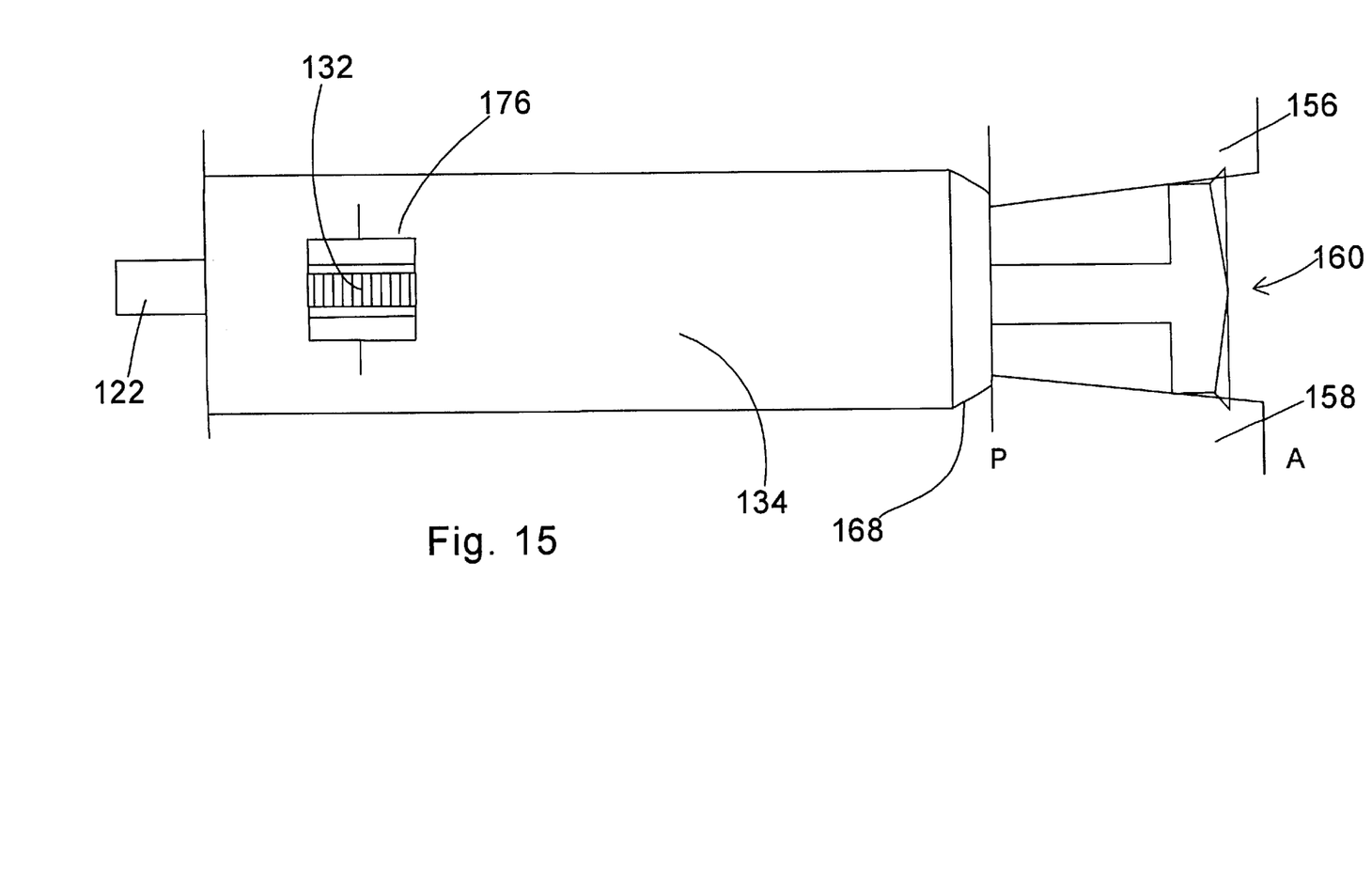
FIG. 15 depicts a side view of the alignment probe of the embodiment of the invention of FIG. 12 inserted between and anchored to the end plates of adjacent vertebral bodies.

Procedurally and preferably for a posterior approach, although probe 122 can be used for an anterior approach, the vertebrae and the disk located therebetween are exposed and some of the disk material is cut away. The alignment probe 122 is then inserted (from the posterior side "P" toward the anterior side "A" in FIG. 15) between the end plates of the vertebral bodies 156, 158, which span the disk 160 space. Using appropriate imaging techniques, the probe 122 is viewed to ensure that the depth of the head end 124 is proper and that the post 126 is properly aligned with the disk space and the adjacent vertebrae. The handle 128 is then used to give the head end 124 a quarter turn so that the ends 146, 152 of the head end 124 are anchored in the upper and lower vertebral bone as shown in FIG. 15. As this occurs, the cam surfaces 147, 153 urge the vertebral bodies 156, 158 apart in order to increase the anterior disk space and return, as desired, the natural lardosis to the spine.

Figure 14:
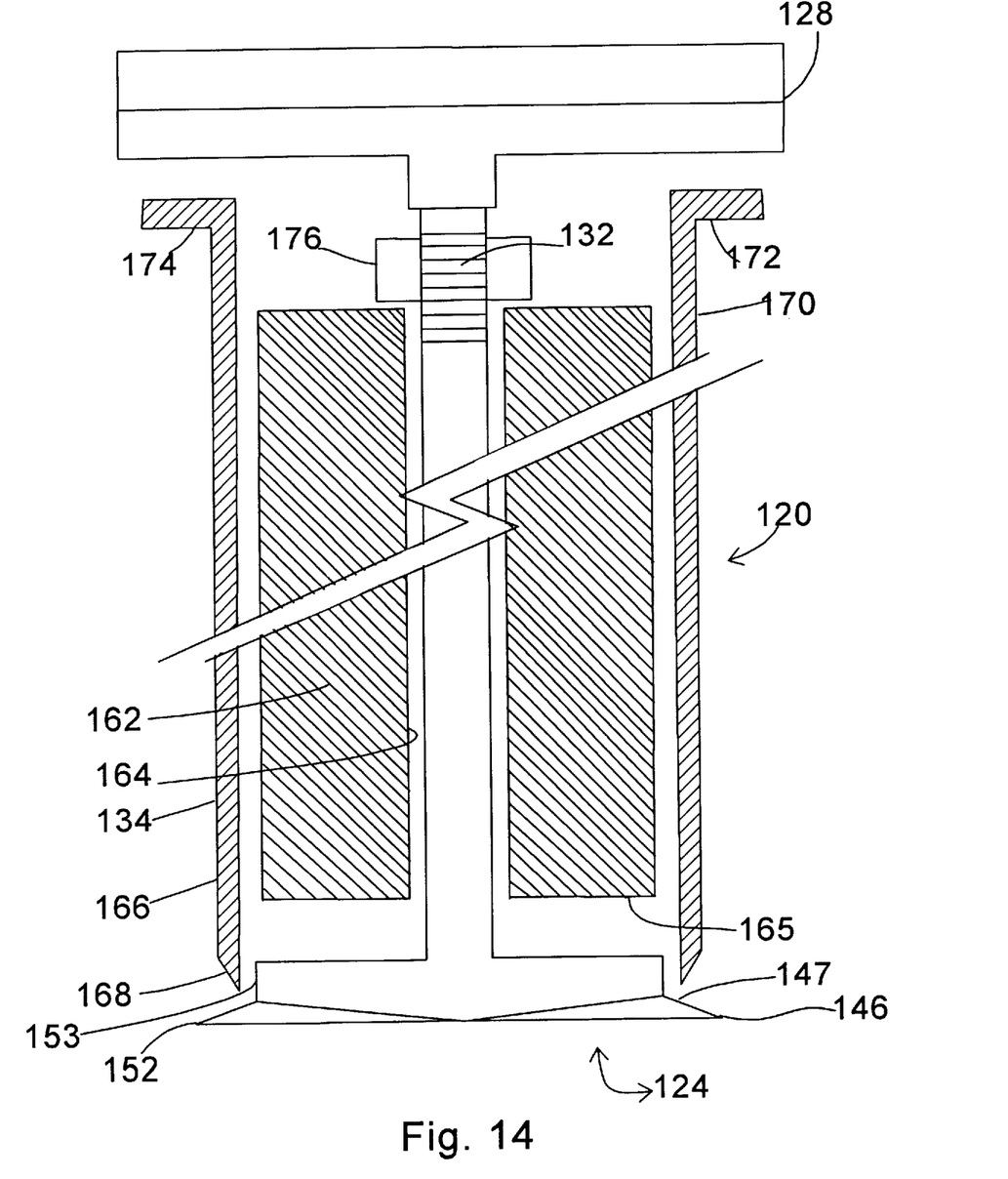
FIG. 14 depicts a partially sectioned cross-section view of the alignment probe of FIG. 12, with a spacer and a cutter of this embodiment of the invention.

After this is accomplished, the handle 128 is removed from the post 126 and a cylindrical spacer 162 with a central bore 164 and tip 165 is placed over the post 126 as shown in FIG. 14. With the spacer so positioned, cutter 134 can be inserted over the spacer and the post 126 of the alignment probe 122 as shown in FIGS. 14, 15 and then positioned against the faces of the vertebral bodies 156 and 158. It is to be understood, that alternatively, the spacer 162 can be incorporated and become an integral part of the cutter 134 and be within the spirit and scope of the invention.

The cutter 134 includes a front end 166 with a sharpened edge 168 and a back end 170 with flanges 172, 174. With the cutter 134 so positioned as seen in FIG. 15, the flanges can be tapped. When this occurs, the cutter cuts through the bone of the upper and lower vertebral bodies and the disk material located therebetween, and proceeds toward the head end 124. The depth of the cutter 134 can be judged by the indicia 132 of the alignment probe 122 as viewed the through the window 176 of the cutter 134. The forward motion of the cutter 134 is stopped by gaging the depth of the cutter relative to the indicia 132 or by the sharpened tips 146, 152 of the head end 124 of the alignment probe 122. After this is accomplished, the alignment probe 122 is given another quarter turn freeing the head end 124 from the upper and lower vertebral bodies. At this point, the entire instrument set including the alignment probe 122 and the cutter 134 can be removed with the bone and disk tissue captured therebetween. An appropriately sized and aligned bore for the insertion of a bone or device implant is then completed.

Industrial Applicability

An advantageous apparatus and method have been demonstrated for preparing a site between adjacent bones for implantation of bone or a device. Preferably, the apparatus and method are used to implant a fusion device which is to be located in the disk space between adjacent vertebral bodies. The present invention has the advantage of ease of alignment and secure anchoring so that the alignment is not affected during the process of preparing the implant site. Further, there is no undue clogging of the instrumentation as the bone and disk material are being severed and removed. Finally, as there is no external sheath used in order to provide protection, from for example a drill, the diameter of the instrumentation can be lessened, providing for smaller space requirements and thus potentially less trauma to the body in carrying out this procedure.

Other features, aspects and objects of the invention can be obtained from a review of the figures and the claims.

It is to be understood that other embodiments of the invention can be developed and fall within the spirit and scope of the invention and claims.

We claim:

1. An instrument set for forming a bore between adjacent spaced bones comprising:

an alignment probe with a head end mounted on a post;

said head end including a first arm and a second arm;

said first arm having a first sharpened tip, and said second arm having a second sharpened tip;

a first cam surface located behind the first sharpened tip and a second cam surface located behind the second sharpened tip; and a cutter which fits over said post and which has a distal cutting edge.

2. The instrument set of claim 1 wherein:

said cutting edge describes a width; and said width is greater than a distance between the first cam surface and the second cam surface, but less than the combined length of said first arm and said second arm such that said first arm and said second arm provide a stop for said cutter.

3. An alignment probe for establishing a desired alignment between spaced bones comprising:

a head end mounted on a post;

said head end including a first arm and a second arm;

said first arm having a first sharpened tip, and said second arm having a second sharpened tip;

a first cam surface located behind the first sharpened tip and a second cam are configured to surface located behind the second sharpened tip; and wherein said first and second cam surfaces cam the spaced bones apart as said probe is rotated relative to said bones and said first and second sharpened tips are cofigured to penetrate the respective spaced bones as the probe is rotated in order to fix the position of the probe relative to the bones.

4. The alignment probe of claim 3 wherein:

said first arm and said second arm together describe a length of between about thirteen millimeters and about twenty-one millimeters.

5. The alignment probe of claim 3 wherein:

said first arm and said second arm together describe a length of one of about thirteen millimeters, about seventeen millimeters, and about twenty-one millimeters.

6. A method for forming a bore between first and second bones comprising the steps of:

selecting an alignment probe which alignment probe comprises:

a head end mounted on a post;

said head end including a first arm with a first sharpened tip and a second arm with a second sharpened tip;

positioning the alignment probe with the first arm and the second arm between the two bones;

twisting the alignment probe so that first sharpened tip of the first arm is secured in the first bone and second sharpened tip of the second arm is secured in the second bone and so that the first cam surface contacts and urges the first bone away from the second bone and the second cam surface contacts and urges the second bone away from the first bone;

placing a cutter over the post, which cutter has a distal cutting edge;

operating the cutter in order to cut into the first bone and the second bone in order to define a bore; and removing the alignment probe and the cutter with the cut bone.

7. The method of claim 6 including the steps of:

performing the operating step until the cutter moves past the first and second cam surfaces and comes into contact with the first and second sharpened tips of the alignment probe.

8. The method of claim 6 including the step of:

said positioning step includes aligning the post of the alignment probe relative to the first bone and the second bone prior to twisting the alignment probe.

9. The method of claim 6 including the step of:

using an imaging instrument during the positioning step to align the post of the alignment probe relative to the first bone and the second bone prior to twisting the alignment probe.

10. The method of claim 6 wherein the first and second bones are first and second vertebrae and wherein:

said positioning step includes positioning said first arm and said second arm of said alignment tool in the disk space between the first and second vertebrae.

11. The method of claim 6 including the step of:

removing disk material from between the first and second vertebrae prior to positioning the first arm and the second arm of the alignment tool in the disk space.

12. The alignment probe of claim 3 wherein said probe is for providing alignment relative to a first vertebra and a second vertebra so that a bore can be created in order to introduce an implant into the disk space between the first vertebra and the second vertebra such that the implant spans the disk space and projects into and engages the first vertebra and the second vertebra.

13. The alignment probe of claim 3 wherein:

said head end has a length of about 13 millimeters to about 21 millimeters.

14. The alignment probe of claim 3 wherein:

said head end has a length selected from one of about 13 millimeters, about 17 millimeters, and about 21 millimeters.

15. The instrument set of claim 1 including:

a spacer with a central bore which fits over said post; and wherein said cutter fits over said spacer and is configured for guidance by said spacer and said alignment probe to a location relative to said spaced bones.

16. The alignment probe of claim 1 for providing alignment between a first vertebra and a second vertebra so that a bore can be created in order to introduce an implant in the disk space between the first vertebra and the second vertebra such that the implant spans the disk space and projects into and engages the first vertebra and the second vertebra, and wherein:

said head end is sized so that it can fit into the disk space between the first vertebra and the second vertebra prior to engaging the first vertebra and the second vertebra.

17. The alignment probe of claim 3 wherein:

said first and second sharpened tips are adapted to prevent a cutter from penetrating the bone to a depth that is past said first and second sharpened tips.

18. The alignment probe of claim 3 wherein:

said first cam surface is located about three millimeters to about five millimeters behind the first sharpened tip, and said second cam surface is located about three millimeters to about five millimeters behind the second sharpened tip.

* * * * *